United States Patent
Giselbrecht et al.

[11] Patent Number: 5,952,206
[45] Date of Patent: Sep. 14, 1999

[54] PROCESS FOR PREPARING L-ASPARTIC ACID

[75] Inventors: Karl-Heinz Giselbrecht, Pasching; Josef Schaller, Linz, both of Austria

[73] Assignee: DSM Fine Chemicals Austria GmbH, Australia

[21] Appl. No.: 09/222,350

[22] Filed: Dec. 29, 1998

[30] Foreign Application Priority Data

Dec. 29, 1997 [AT] Austria ................................ 2191/97

[51] Int. Cl.⁶ .................................................... C12P 13/22
[52] U.S. Cl. ............................................................ 435/109
[58] Field of Search ............................................. 435/109

[56] References Cited

U.S. PATENT DOCUMENTS

| | | | |
|---|---|---|---|
| 4,326,029 | 4/1982 | Yukawa et al. | 435/109 |
| 4,560,653 | 12/1985 | Sherwin et al. | 435/109 |
| 4,692,409 | 9/1987 | Kisumi et al. | 435/109 |
| 5,541,090 | 7/1996 | Sakano et al. | 435/109 |
| 5,741,681 | 4/1998 | Kato et al. | 435/109 |

*Primary Examiner*—Herbert J. Lilling
*Attorney, Agent, or Firm*—Wenderoth, Lind & Ponack, L.L.P.

[57] ABSTRACT

An improved process for preparing L-aspartic acid by enzyme-catalyzed reaction of fumaric acid with ammonia, in which, after reaction has been completed, excess ammonia is removed from the reaction mixture, L-aspartic acid is precipitated by adding acetic acid or formic acid, whereupon formic acid and acetic acid are rereleased from the mother liquor by adding fumaric acid, and the ammonia released and the liberated formic or acetic acid and the ammonium fumarate formed in the liberation are reused for subsequent cycles.

10 Claims, 1 Drawing Sheet

PROCESS FOR PREPARING L-ASPARTIC ACID

L-Aspartic acid is an essential starting material for a wide variety of additives for the pharmaceutical industry and the food sector. For example, L-aspartic acid is used for preparing artificial sweetener, for example aspartame. A multiplicity of chemical and enzymatic processes have therefore already been described for the preparation of L-aspartic acid. In the case of the enzymatic variants, L-aspartic acid is usually produced by enzymatic addition of ammonia to fumaric acid with subsequent precipitation from the resulting ammonium L-aspartate solution.

L-Aspartic acid can be precipitated, for example, by adding a mineral acid, such as sulfuric acid or hydrochloric acid, or other acids, such as p-toluenesulfonic acid.

However, the disadvantages of this are that the loss of ammonia is high and a large amount of wastewater having a high concentration of ammonium salts of the acids used is discharged.

For this reason, attempts have been made to find possible methods of reducing or eliminating entirely the problems of wastewater.

According to U.S. Pat. No. 4,560,653, L-aspartic acid is precipitated, for example, by the addition of maleic acid. Following the separation of L-aspartic acid, the remaining mother liquor is subjected to an isomerization step, in which maleic acid is isomerized into fumaric acid, for example by means of a catalyst containing bromide ions, then purified and returned to the enzymatic reaction.

To bypass the isomerization step, other suitable additives to precipitate out L-aspartic acid have been sought.

Japanese Laid-Open Application JP 08-33493 (Chem. Abstracts 1224: 315 167) describes the use of fumaric acid or fumarate salt as precipitant. The disadvantage of this process variant is the poor water solubility of fumaric acid, as a result of which, in the workup of the mother liquor, either large volumes of water have to be distilled off, or a very dilute procedure involving large reaction volumes is necessary.

The object of the invention was therefore to find a process which avoids the previous problems with the precipitation of L-aspartic acid and which leads to L-aspartic acid in high yields and high purity.

Unexpectedly, this object has been achieved by using formic acid or acetic acid as precipitant and circulating all reaction streams.

The invention therefore relates to an improved process for preparing L-aspartic acid by enzyme-catalyzed reaction of fumaric acid with ammonia, which comprises a) reacting fumaric acid with ammonia in an inert diluent in the presence of aspartase or aspartase-producing microorganisms to give ammonium L-aspartate, then b) removing ammonia from the reaction mixture and c) precipitating L-aspartic acid from the remaining reaction mixture by adding formic acid or acetic acid, then separating off, washing and drying the L-aspartic acid, and d) releasing formic acid or acetic acid from the mother liquor containing ammonium formate or acetate, respectively, combined with the wash water, by adding fumaric acid, e) after filtration of the resulting ammonium fumarate solution, using the filtrate again supplying, with or without fresh formic acid or acetic acid, in step c) to precipitate out L-aspartic acid and f) mixing the remaining ammonium fumarate with the ammonia from step b) and adding this mixture as starting material to step a).

Figure 1:
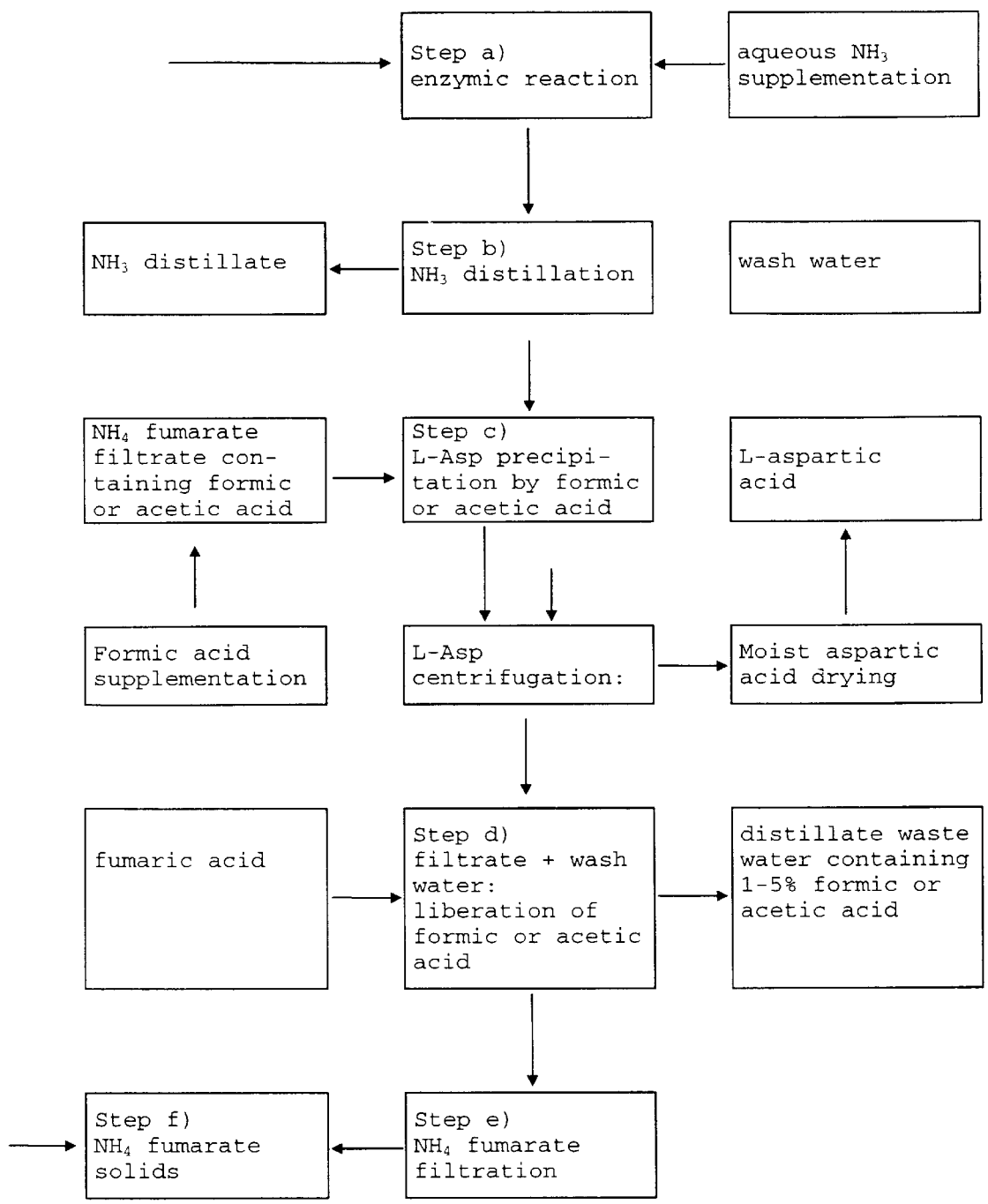
FIG. 1 depicts a flow sheet of the process according to the present invention.

In the process according to the invention, L-aspartic acid is precipitated out using formic acid or acetic acid. The reaction streams are all circulated according to the invention. The process according to the invention is shown in FIG. 1, in which the reaction streams are depicted diagrammatically.

The first step of the process according to the invention comprises the enzymatic reaction of fumaric acid with ammonia. The reaction takes place in an inert diluent. Suitable inert diluents are water, water/ethanol or water/acetone mixtures and the like. Preferably, water is used. Fumaric acid can be used in this step in a concentration up to the solubility limit, so that either a solution or a suspension is obtained. Into this solution or suspension, ammonia in gaseous or liquefied form or in the form of a 10 to 35% strength by weight solution is introduced, which raises the temperature to 60° C. and establishes a pH between 7 and 9.

Preferably, an aqueous 20 to 30% strength by weight ammonia solution is used. Then, into the resulting system, preferably a solution, the enzyme aspartase or an aspartase-producing microorganism is stirred at 20 to 60° C., preferably at 30 to 50° C. For this addition of enzyme or aspartase-producing microorganism, it is advantageous if a solution is produced by the addition of ammonia, since in the case of a suspension more enzyme is required owing to adsorption of the enzyme and the resulting loss in activity. For a virtually quantitative conversion after up to 24 to 30 hours, 30 to 50 IU (enzyme activity) are required per mole of fumaric acid.

Aspartase-producing microorganisms are, for example, *Pseudomonas fluorescens, Protens vulgaris, Pseudomonas aeruginosa, Serratia marcescens, Bacterium succinium, Bacillus subtilis, Aerobacter aerogenes,* Micrococcus sp., *Escherichia coli,* et cetera.

Other suitable aspartase-producing microorganisms are described, for example, in U.S. Pat. No. 3,791,926 and U.S. Pat. No. 3,198,712.

In the process according to the invention, furthermore, purified or synthetic aspartase can be used. The enzyme or the aspartase-producing microorganism can be added in liquid or immobilized form as described, for example, in EP 0 127 940.

After the reaction is complete—the end of the reaction can be determined photometrically, for example—ammonia is separated off in accordance with step b) by distillation or stripping.

Step b) can be performed at atmospheric pressure or at reduced pressure and at temperatures of 30 to 110° C., preferably 40 to 90° C.

Excess ammonia is removed from the reaction mixture in this step using familiar distillation methods, for example using short-path or thin-layer evaporators, strippers, etc. Depending on the distillation method, either, preferably, atmospheric pressure or reduced pressure between 80 and 200 mbar is employed here. The resulting ammonia distillate is reused in a subsequent process step, step f), or is reused as starting material for a subsequent enzymic reaction a).

After the removal of ammonia, in step c) the L-aspartic acid is precipitated out.

For this purpose, formic acid or acetic acid is added to the monoammonium L-aspartate solution, which was obtained by removing the ammonia, in a molar ratio of monoammonium L-aspartate to formic acid or acetic acid of 1:0.8 to 2, preferably 1:1 to 1.2. Preferably, formic acid is used as precipitant. The pH during the precipitation is preferably between 4 and 6.

From the 2nd reaction cycle on, ammonium fumarate filtrate (obtained from the subsequent step e)), which comprises the released formic acid or acetic acid, is added as precipitant to the monoammonium L-aspartate solution. To achieve the desired molar ratio of aspartate to precipitant, the filtrate may be supplemented with formic acid or acetic acid.

The reaction temperature is between 0 and 95° C., preferably between 20 and 90° C., particularly preferably between 40 and 70° C. The L-aspartic acid which crystallizes out is then filtered off from the reaction mixture, for example by absorption filtration or centrifugation. Preferably, L-aspartic acid is separated off by centrifugation. The filtration temperature is between 10 and 70° C., preferably between 15 and 50° C. The L-aspartic acid crystals filtered off are finally washed, preferably with water, and dried. Owing to the very high solubility of ammonium formate or acetate, only a very little wash water is necessary to wash the freshly precipitated L-aspartic acid. L-Aspartic acid can thus also be washed at relatively low temperatures. If L-aspartic acid comprises ammonium fumarate owing to the use of fumaric acid as precipitant, in contrast, higher wash temperatures and wash water volumes are necessary.

The remaining filtrate obtained after removing L-aspartic acid, and the wash water produced during the washing, are combined, if appropriate concentrated by evaporation to half the volume, admixed with fumaric acid and heated to boiling temperature, under reduced pressure or at atmospheric pressure, depending on the distillation method chosen, to rerelease the formic acid or acetic acid.

Preferably, the fumaric acid is added at a maximum of 100° C., particularly preferably at a maximum of 70°C. Distillate water is distilled off in this case together with a small part, about 1 to 5 mol%, of the formic acid or acetic acid.

The remaining solution is filtered or centrifuged and the ammonium fumarate filtrate, containing the majority of the formic acid or acetic acid, is, from the second cycle on, reused in step c) to precipitate out L-aspartic acid.

For this purpose, the amount distilled off in the release of the acid may be supplemented by adding fresh formic acid or acetic acid.

The remaining ammonium fumarate solid, in contrast, is combined with the ammonia distilled off in step b) and, from the second cycle on, is added to the enzyme-catalyzed reaction as starting material in step a). At the same time, the deficient amount of ammonia is supplemented by adding ammonia, preferably in the form of a 10 to 35% strength by weight solution, so that a pH between 7 and 9 is again established.

Any ammonium formate present does not interfere with the enzymic reaction.

By means of the process according to the invention, L-aspartic acid is produced in a yield greater than 80%, up to 95% and at a purity of greater than 99.5%.

EXAMPLE 1

From 900 ml (955 g) of L-aspartic acid reaction solution (DSM-Chemie Linz) comprising 240.6 g (1.80 mol) of L-aspartic acid, prepared by reaction of 210 g (1.8 mol) of fumaric acid with 406 ml of 25% strength by weight ammonia solution (336 g) in 420 ml of $H_2O$ in the presence of 0.15 ml of aspartase solution (1000 IU/ml), 526 g of $NH_4OH$ were distilled off on the rotary evaporator at 75° C. and 150 mbar. The bottom phase was diluted to 955 g with distilled $H_2O$, enzyme residues were filtered off with suction, and 82.8 g (1.8 mol) of formic acid were added at 85° C. (pH 5.5). After 15 minutes, the precipitate was separated off from the supernatant solution at 85° C. 251.9 g of solids (F1) and 744 g of mother liquor 1 (moli 1) were obtained.

The mother liquor (moli 1) was cooled to room temperature and separated off from the solid precipitating out in the course of this. This produced 51.7 g of solids (F 1.1) and 678.5 g of mother liquor (moli 1.1).

The two quantities of solids were combined, combined with 250 ml of distilled $H_2O$, heated to reflux and cooled to room temperature and the precipitated solids were separated off from the mother liquor.

moli 2: 191 g

F2: 288.0 g (containing 30.1% $H_2O$)

F2 was in turn admixed with 250 ml of $H_2O$, again heated to reflux temperature and then cooled to room temperature.

moli 3: 244 g

F3: 286.3 g (containing 33.4% $H_2O$)

F3 was dried at 70°C. and full vacuum, which produced 195.2 g (=81.5% of theory) of L-aspartic acid (containing 0.1% $H_2O$).

To work up the mother liquors, all batches (moli 1, 1.1, 2 and 3) were combined (1130 g, 1060 ml) and 525 ml of $H_2O$ were distilled off on the rotary evaporator at 70° C. and approximately 150 mbar. The bottom phase (565 g) was admixed with 210 g (1.8 mol) of fumaric acid and heated to boiling temperature (102° C.), which dissolved all of the solids.

Vacuum distillation was then carried out at 100 mbar and a reflux ratio of 5:1.

Distillate 1: 100 g bottom temperature 48.5°C.
top temperature 46.8°C.

Distillate 2: 102 g bottom temperature 48.5°C.
top temperature 48.8°C.

Distillation was continued with total takeoff. In total, 1823 g of distillate were obtained.

The remaining bottom phase was cooled to room temperature and the precipitated solids were filtered off with suction.

moli 4: 543.8 g

F4: 360 g (18% $H_2O$)

F4 (equivalent to 2.1 mol of fumaric acid) was then dissolved in 441 g of distilled $H_2O$, admixed with 353.5 g (2.1 mol) of 25% strength ammonia (pH 9.3), and allowed to react in the presence of 0.15 g of aspartase for 24 hours at 50° C. in a drying cabinet. A conversion rate of 99.1% was achieved.

EXAMPLE 2

Reaction cycle 1:

The 1st cycle was carried out in a similar manner to Example 1.

In turn, 195 g of L-aspartic acid (0.1% $H_2O$) were obtained (81.5% of theory).

The formic acid content was 0.1%, and the fumaric acid content 0.3%. To work up the mother liquors, again, all batches were combined and 525 g were distilled off at 70° C. and approximately 150 mbar.

565 g of bottom phase were again admixed with 210 g (1.8 mol) of fumaric acid, heated to boiling temperature (102° C.) and cooled to 10° C. and the precipitate was separated off.

369 g of moli 4 were obtained. The solids (F4) were washed on the suction filter with 100 ml of distilled $H_2O$.

F4: 367.8 g (32.6% $H_2O$)

Wash water (W4): 115 g

Reaction cycle 2: 367.8 g of F4 were admixed with 450 g of distilled $H_2O$ and 238.2 g (3.4 mol) of 25% strength aqueous ammonia and reacted in the presence of 0.13 g of aspartase at pH 8.7 and 50° C. for 72 hours in a drying cabinet.

The resulting reaction solution (1050 g, 945 ml) was then concentrated to about half the volume at 70° C. and approximately 150 mbar.

587.5 g of distillate 450 g of bottom phase (enzyme residues were filtered off, pH 5.4).

The bottom phase was heated to 80° C. and was admixed as rapidly as possible with a mixture of moli 4 and W4 from reaction cycle 1 and 14 g (17%) of fresh formic acid (pH 5.3).

The mixture was cooled to 10° C. in the course of this. The precipitated solids (F5) were then centrifuged off and washed with 200 ml of $H_2O$ (W5).

moli 5: 606 g

W5: 203 g

F5: 262.4 g (40.4% $H_2O$)

F5 was dried at 75° C. and in vacuo.

154.2 g (64.6% of theory) of L-aspartic acid were obtained (formic acid content 0.1%, fumaric acid content 0.3%).

Moli 5 and W5 (791 g) were combined and concentrated at 70° C. and approximately 150 mbar.

The remaining bottom phase (500 g) was heated to 80° C. and slowly admixed with 210 g (1.8 mol) of fumaric acid, heated to reflux (105° C.), diluted with 300 ml of distilled $H_2O$ to produce a solution (T 101° C.) and then cooled to room temperature. The precipitated solids (F6) were centrifuged off and washed.

moli 6: 634 g

W6: 104 g

F6: 296 g (12.3% $H_2O$)

Reaction cycle 3:

F6 from reaction cycle 2 was admixed with 587 g of ammonia distillate from reaction cycle 2 and 177 g (2.52 mol) of fresh ammonia and reacted in the presence of 0.2 ml of enzyme at 50° C. for 24 hours in a drying cabinet (98.4% conversion rate). The resulting reaction solution (1015 g) was concentrated to about half the volume at 70° C. and approximately 150 mbar (distillate: 481 g).

The remaining bottom phase (526 g), after removal of enzyme residues by filtration, was heated to 65° C. and slowly admixed with 738 g of a mixture of moli 6 and w6.

The mixture was then stirred for 2 hours at 65° C. and cooled to 10° C. and the precipitated solids (F7) were centrifuged off and washed with 200 ml of $H_2O$ (W7).

moli 7: 1019 g

W7: 200 g

F7: 168 g (7.7% $H_2O$)

F7 was dried in vacuo at 75° C.

154.2 g (64.4% of theory) of L-aspartic acid were obtained.

Moli 7 and W7 were combined and concentrated at 70° C. and 150 mbar.

504.6 g of bottom phase were then heated to 70° C., admixed with 210 g (1.8 mol) of fumaric acid and 100 ml of $H_2O$, stirred for 2 h and cooled to room temperature and the precipitated solids (F8) were centrifuged off and washed (W8).

Moli 8: 337 g

W8: 196.4 g

F8: 404 g (18.5% $H_2O$)

Reaction cycle 4:

404g of F8 were admixed with 481 g of ammonia distillate from cycle 3 and 177 g of fresh ammonia and allowed to react together with 0.2 ml of enzyme at pH 8.7 and 50° C. for 24 h (98.7 conversion rate).

The workup steps were performed in a similar manner to cycles 1–3.

315 g (131.8% of theory) of L-aspartic acid were obtained.

Finally, a 5th cycle was carried out in a similar manner to reaction cycles 1–4.

The mass balance of the 5 cycles can be seen in Table 1.

TABLE 1

| | Fum. A (mol) | $NH_4Fum$ (mol) | $NH_3$ (mol) | For.A (mol) | L-Asp. (mol) | L-Asp. (yield %) | pH L-Asp precipitation |
|---|---|---|---|---|---|---|---|
| 1st cycle | 1.80 | 1.80 | 4.32 | 1.80 | 1.46 | 81.50 | 5.5 |
| 2nd cycle | 1.80 | 1.85 | 3.40 | 0.30 | 1.15 | 64.40 | 5.3 |
| 3rd cycle | 1.80 | 1.95 | 2.50 | 0.00 | 1.10 | 62.60 | 5.0 |
| 4th cycle | 1.80 | 2.47 | 3.00 | 1.80 | 2.36 | 131.80 | 4.4 |
| 5th cycle | 1.80 | 1.84 | 3.00 | 0.00 | 1.81 | 100.80 | 4.4 |
| Total | 9.00 | 9.91 | 16.22 | 3.90 | 7.89 | 88.58 | |

Fum.A: fumaric acid
$NH_4$Fum.: ammonium fumarate
For.A: formic acid
L-Asp: L-aspartic acid

We claim:

1. An improved process for preparing L-aspartic acid by enzyme-catalyzed reaction of fumaric acid with ammonia, which comprises a) reacting fumaric acid with ammonia in an inert diluent in the presence of aspartase or aspartase-producing microorganisms to give ammonium L-aspartate, then b) removing ammonia from the reaction mixture and c) precipitating L-aspartic acid from the remaining reaction mixture by adding formic acid or acetic acid, then separating off, washing and drying the L-aspartic acid, and d) releasing formic acid or acetic acid from the mother liquor containing ammonium formate or acetate, respectively, combined with the wash water, by adding fumaric acid, e) after filtration of the resulting ammonium fumarate solution, using the filtrate again, with or without fresh formic acid or acetic acid, in step c) to precipitate out L-aspartic acid and f) mixing the remaining ammonium fumarate with the ammonia from step b) and adding this mixture as starting material to step a).

2. The process as claimed in claim 1, wherein the diluent used in step a) is water, water/ethanol mixture or water/acetone mixture.

3. The process as claimed in claim 1, wherein step a) is carried out at a pH between 7 and 9.

4. The process as claimed in claim 1, wherein, in step b), distillation is carried out at temperatures between 30 and 110° C. and at atmospheric pressure or reduced pressure.

5. The process as claimed in claim 1, wherein, in step b), ammonia is distilled off by means of a stripper, short-path evaporator or thin-film evaporator.

6. The process as claimed in claim 1, wherein step c) is carried out at a pH between 4 and 6.

7. The process as claimed in claim 1, wherein step c) is carried out at a temperature between 0 and 95° C.

8. The process as claimed in claim 1, wherein, in step d), fumaric acid is added at a maximum of 100° C.

9. The process as claimed in claim 1, wherein the mixture obtained in step f) of ammonium formate and ammonia from step b) is supplemented with ammonia until a pH between 7 and 9 is reached and is used as starting material in step a).

10. The process as claimed in claim 8, wherein the fumaric acid is added at a maximum of 70° C.

* * * * *

UNITED STATES PATENT AND TRADEMARK OFFICE
CERTIFICATE OF CORRECTION

PATENT NO. : 5,952,206
DATED : September 29, 1999
INVENTOR(S) : Karl-Heinz GISELBRECHT et al.

It is certified that error appears in the above-identified patent and that said Letters Patent is hereby corrected as shown below:

On the title page: item [73], the Assignee's nationality "Australia" should read --Austria--.

Signed and Sealed this

Fifteenth Day of August, 2000

Q. TODD DICKINSON

Attest:

Attesting Officer

Director of Patents and Trademarks